(12) United States Patent
Mac Dermott et al.

(10) Patent No.: US 10,130,565 B2
(45) Date of Patent: Nov. 20, 2018

(54) SOLID COSMETIC COMPOSITION IN COMPACT POWDER FORM

(75) Inventors: Padraig Mac Dermott, Meudon (FR); Mickael Bailleul, La Norville (FR); Gwenola Le Gars, Paris (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/118,758

(22) PCT Filed: May 30, 2012

(86) PCT No.: PCT/EP2012/060180
§ 371 (c)(1),
(2), (4) Date: Nov. 19, 2013

(87) PCT Pub. No.: WO2012/163984
PCT Pub. Date: Dec. 6, 2012

(65) Prior Publication Data
US 2014/0093461 A1    Apr. 3, 2014

Related U.S. Application Data

(60) Provisional application No. 61/493,990, filed on Jun. 7, 2011.

(30) Foreign Application Priority Data

May 31, 2011    (FR) ...................... 11 54759

(51) Int. Cl.
| | |
|---|---|
| A61K 8/90 | (2006.01) |
| A61K 8/02 | (2006.01) |
| A61Q 1/12 | (2006.01) |
| A61Q 1/10 | (2006.01) |
| A61K 8/25 | (2006.01) |
| A61K 8/98 | (2006.01) |
| A61Q 1/08 | (2006.01) |

(52) U.S. Cl.
CPC ............... *A61K 8/022* (2013.01); *A61K 8/25* (2013.01); *A61K 8/90* (2013.01); *A61K 8/987* (2013.01); *A61Q 1/08* (2013.01); *A61Q 1/10* (2013.01); *A61Q 1/12* (2013.01)

(58) Field of Classification Search
CPC ............... A61K 8/0241; A61K 8/0216
See application file for complete search history.

(56) References Cited

U.S. PATENT DOCUMENTS

| | | | |
|---|---|---|---|
| 6,083,516 A | 7/2000 | Curtis et al. | |
| 2003/0232030 A1* | 12/2003 | Lu | A61K 8/39 424/70.122 |
| 2005/0142089 A1* | 6/2005 | Lu | A61K 8/585 424/70.7 |
| 2009/0142382 A1* | 6/2009 | Shah et al. | 424/401 |
| 2010/0242984 A1* | 9/2010 | Arditty | A45D 40/26 132/218 |
| 2012/0164091 A1* | 6/2012 | Cruz | A61Q 1/12 424/69 |

FOREIGN PATENT DOCUMENTS

| | | |
|---|---|---|
| CN | 1225259 A | 8/1999 |
| EP | 0 497 144 A1 | 8/1992 |
| FR | 2 735 692 | 12/1996 |
| WO | WO 03/061611 A2 | 7/2003 |
| WO | WO 2012/087453 | 6/2012 |

OTHER PUBLICATIONS

Kraton Polymers Catalogue.*
International Search Report dated Jun. 2, 2014 in PCT/EP2012/060180.
French Preliminary Search Report dated May 8, 2012 in Patent Application No. 1154759 (with English translation of Categories of Cited Documents).
Office Action in corresponding European application No. 12729049.2-1458, dated Jun. 6, 2016.
Notice of Reasons for Rejection in corresponding Japanese Application No. 2014-513178, dated Mar. 7, 2016.
Office Action dated Mar. 6, 2017, in Chinese Patent Application No. 201280024629.9 (PCT/EP2012/060180).

* cited by examiner

*Primary Examiner* — Micah Paul Young
(74) *Attorney, Agent, or Firm* — Oblon, McClelland, Maier & Neustadt, L.L.P.

(57) ABSTRACT

The present invention relates to a solid cosmetic composition in the form of a compact powder, comprising, in a physiologically acceptable medium, at least: —a pulverulent phase in an amount of greater than or equal to 35% by weight relative to the total weight of the composition, —a liquid fatty phase comprising at least one non-volatile oil, and —at least one amorphous hydrocarbon-based block copolymer. The present invention also relates to a process for coating the face, and in particular the eyelids, with the said cosmetic composition.

21 Claims, No Drawings

SOLID COSMETIC COMPOSITION IN COMPACT POWDER FORM

The present invention targets the field of care and/or makeup solid cosmetic compositions, and more specifically compositions in compact powder form. The invention also relates to a process for coating the skin, and in particular the eyelids, with the said cosmetic composition.

The galenical forms conventionally adopted for solid compositions are generally loose, pressed or compact powders. As non-limiting illustrations of the solid galenical forms more particularly considered in the field of makeup, mention may be made especially of loose or pressed powders such as foundation powders, face powders and eyeshadows.

The function of the abovementioned powders is mainly to give colour, mattness and even, for those more particularly intended for facial skin, to improve the wear properties of a foundation or, if used alone, to give coverage.

These galenical forms are particularly appreciated by users with regard to their lightness, softness, tack-free aspect or non-greasy feel.

In general, these compositions combine a pulverulent phase that is generally predominant with a binder phase usually featured by a liquid fatty phase. The pulverulent phase is formed essentially of fillers combined with colouring agents, the amount of these colouring agents being modified to afford the desired makeup effect, generally a colour effect.

To obtain a composition in compact solid form, it is known from the prior art to use pressed or compacted makeup powders formed by a mixture of powders with a fatty binder, which are put in form, for example, by pressing (at about 10 bar) or compacting (at about 100 bar).

However, these powders may have the drawback of being fragile. Thus, when the percentage of pigments or nacres increases in the product, its manufacture and its pressing or compacting become complicated or even impossible to perform at an industrial level given the quality and productivity requirements.

In addition, compacted powders may be brittle and may have poor impact strength. For example, compositions having a nacre content of greater than or equal to 30% have the drawback of being more fragile and thus of breaking more easily in the event of impacts. This problem is also encountered when high contents of lamellar compounds such as fillers are used.

To do this, one solution consists in increasing the amount of fatty binder, but this composition will then have a tendency to become waxy, i.e. to harden during use to the point that it cannot be taken up. Such compositions are also extremely difficult to compact, as a result of which pressing is quite often performed under lower pressing conditions. However, once pressed, these compositions remain fragile and have a tendency to disintegrate or even to break, for example when the product is dropped.

One aim of the present invention is thus to obtain makeup compositions in the form of compact and preferably pressed powders, which show good cohesion and good homogenization, while at the same time offering satisfactory cosmetic qualities, thus allowing a uniform makeup result, and/or without any overthickness or any material effect.

One aim of the present invention is also to obtain compositions that do not become waxy over time, thus conserving their uptake qualities.

One aim of the present invention is also to obtain compositions that do not crack over time.

One aim of the present invention is also to obtain impact-resistant makeup compositions in the form of compact and preferably pressed powders.

One aim of the present invention is also to obtain makeup compositions in the form of compact and preferably pressed powders, which show good adhesion to the keratin material to be made up, in particular the eyelids, in particular good wear properties over time (for example eight hours) and with respect to water or rubbing.

One aim of the present invention is also to make a composition that is comfortable on application, i.e. which does not pull on the applied skin surface.

To do this, according to a first aspect, one subject of the present invention is a solid makeup and/or care cosmetic composition in the form of a compact and preferably pressed powder, comprising, in a physiologically acceptable medium, at least:
- a pulverulent phase in an amount of greater than or equal to 35% by weight relative to the total weight of the composition,
- a liquid fatty phase comprising at least one non-volatile oil, and
- at least one amorphous hydrocarbon-based block copolymer.

Such a composition is preferably obtained via a pressing manufacturing process.

Such a composition may thus make it possible to formulate eye shadows containing a large amount of colouring agents such as pigments and/or nacres, in particular nacres.

Such a composition may thus make it possible to formulate eye shadows containing, for example, more than 50% by weight of colouring agents, and preferably more than 50% of nacres, relative to the total weight of the composition, without embrittling the product, and while conserving good uptake qualities.

The texture of such a composition allows the application to the skin of a smooth, uniform film, which has good wear properties.

Finally, despite the possible presence of a large amount of lamellar compounds (nacres or fillers), this composition remains particularly resistant to impacts.

The composition according to the invention preferably comprises as pulverulent phase at least one filler, for example in a content of greater than or equal to 2%.

For the purposes of the present invention, the following definitions apply:
- "solid" means the state of the composition at room temperature (25° C.) and at atmospheric pressure (760 mmHg), i.e. a composition of high consistency, which conserves its form during storage. As opposed to "fluid" compositions, it does not flow under its own weight. It is advantageously characterized by a hardness as defined below.
- "compact powder" means a mass of product whose cohesion is at least partly provided by compacting or, preferably, pressing during the manufacture. In particular, by taking a measurement using a TA.XT.plus Texture Analyser texturometer sold by the company Stable Micro Systems, the compact powder according to the invention may advantageously have a pressure resistance of between 0.1 and 1 kg and especially between 0.2 and 0.8 kg, relative to the surface area of the spindle used (in the present case 7.07 $mm^2$) The measurement of this resistance is performed by moving an SMS P/3 flat-headed cylindrical spindle in contact with the powder over a distance of 2 mm and at a speed of 0.5 mm/second; more generally, this powder may be obtained by compacting or, preferably, by pressing.

"physiologically acceptable medium" is intended to denote a medium that is particularly suitable for the application of a composition according to the invention to the skin.

Preferably, the composition according to the invention comprises less than 3% by weight and preferably less than 2% by weight of water relative to the total weight, or even is free of water.

The composition according to the invention advantageously comprises a solids content of greater than or equal to 95%, better still 98%, or even equal to 100%.

For the purposes of the present invention, the "solids content" denotes the content of non-volatile matter.

The solids content (abbreviated as SC) of a composition according to the invention is measured using a "Halogen Moisture Analyzer HR 73" commercial halogen desiccator from Mettler Toledo. The measurement is performed on the basis of the weight loss of a sample dried by halogen heating, and thus represents the percentage of residual matter once the water and the volatile matter have evaporated off.

This technique is fully described in the machine documentation supplied by Mettler Toledo.

The measuring protocol is as follows:

Approximately 2 g of the composition, referred to hereinbelow as the sample, are spread out on a metal crucible, which is placed in the halogen desiccator mentioned above. The sample is then subjected to a temperature of 105° C. until a constant weight is obtained. The wet mass of the sample, corresponding to its initial mass, and the dry mass of the sample, corresponding to its mass after halogen heating, are measured using a precision balance.

The experimental error associated with the measurement is of the order of plus or minus 2%.

The solids content is calculated in the following manner:

Solids content(expressed as weight percentage)= 100×(dry mass/wet mass).

The composition may comprise a pulverulent phase in an amount of greater than or equal to 50% by weight and better still 60% by weight relative to the total weight of the composition. The pulverulent phase advantageously comprises at least one colouring agent chosen from nacres. This pulverulent phase preferably comprises more generally at least one colouring agent chosen from nacres, pigments and reflective particles, and mixtures thereof. The pulverulent phase advantageously comprises at least one filler and at least one colouring agent chosen in particular from nacres.

The said composition may have a nacre content of greater than or equal to 30%, better still greater than or equal to 40% and even better still 50%. In particular, the said composition has a nacre content of between 30% and 70% by weight and preferably between 40% and 60% by weight relative to the total weight of the composition.

The said composition preferably comprises at least one non-volatile hydrocarbon-based oil. This non-volatile hydrocarbon-based oil preferably comprises at least one $C_{12}$-$C_{15}$ alkyl benzoate.

The said composition advantageously comprises at least one additional non-volatile hydrocarbon-based oil or at least one non-volatile silicone oil, and a mixture or mixtures thereof.

Preferably, the said composition comprises one or more linear or phenylated, preferably phenylated, non-volatile silicone oils. The additional non-volatile oil(s) are present in a (total) content of greater than or equal to 8% by weight relative to the total weight of the composition.

The amorphous hydrocarbon-based block copolymer(s) advantageously comprise an amorphous polymer formed by polymerization of an olefin. The hydrocarbon-based block copolymer(s) advantageously comprise an amorphous block polymer of styrene and of an olefin. The hydrocarbon-based block copolymer(s) advantageously comprise a copolymer, optionally a hydrogenated copolymer, containing styrene blocks and ethylene/$C_3$-$C_4$ alkylene blocks. The hydrocarbon-based block copolymer(s) advantageously comprise a styrene-ethylene/butylene-styrene triblock copolymer. The hydrocarbon-based block copolymer(s) advantageously comprise a blend of a styrene-butylene/ethylene-styrene triblock copolymer and of a styrene-ethylene/butylene diblock copolymer. The hydrocarbon-based block copolymer(s) are present in a total content of greater than or equal to 1% by weight relative to the total weight of the composition, preferably between 1.5% and 4% by weight relative to the total weight of the composition and better still between 2% and 4% by weight relative to the total weight of the composition. The hydrocarbon-based block copolymer(s) and the non-volatile hydrocarbon-based oil(s) chosen from $C_{12}$-$C_{15}$ alkyl benzoates are present in the composition in a respective total content such that the weight ratio of the hydrocarbon-based block copolymer to the said $C_{12}$-$C_{15}$ alkyl benzoates is inclusively between 0.06 and 0.3 and better still between 0.08 and 0.2.

Preferably, the composition according to the invention is an eyeshadow, an eyebrow composition, a blusher or a face powder. Even more preferentially, the composition is chosen from an eyeshadow, a blusher and a powder with a healthy-complexion effect.

According to one particularly preferred embodiment, the said solid makeup and/or care cosmetic composition that is in the form of a compact powder comprises, in a physiologically acceptable medium, limits inclusive and expressed as weight of solids for each of the compounds considered, relative to the total weight of the composition, at least:
  0.5% to 5% of amorphous hydrocarbon-based block copolymer(s),
  30% to 40% of non-volatile hydrocarbon-based oil(s) alone or, preferably, mixed with at least one additional non-volatile silicone oil,
  50% to 70% of colouring agent(s) comprising:
    a) preferably 0.5% to 15% of pigments, chosen in particular from metallic (poly)oxides, preferably iron oxides,
    b) 35% to 60% of nacre(s), chosen in particular from coated micas,
  2% to 10% of filler(s) and
  0% of water.

According to a second aspect, a subject of the present invention is also a process for making up and/or caring for keratin materials, in particular the skin, preferably facial skin and especially the eyelids, in which a composition as defined previously is applied to the said keratin materials.

Pulverulent Phase

The pulverulent phase advantageously comprises fillers and colouring agents.

A solid composition according to the invention advantageously has a content of pulverulent phase of greater than or equal to 35% by weight, in particular greater than or equal to 40% by weight, more particularly ranging from 50% to 80% by weight and better still from 60% to 70% by weight relative to the total weight of the composition.

Fillers

The term "fillers" should be understood as meaning colourless or white solid particles of any form, which are in a form that is insoluble and dispersed in the medium of the composition. Mineral or organic in nature, they make it possible to confer softness, mattness and uniformity of makeup on the composition.

The fillers used in the compositions according to the present invention may be in lamellar, globular or spherical form, in the form of fibres or in any other intermediate form between these defined forms.

The fillers according to the invention may or may not be surface-coated, and in particular they may be surface-treated with silicones, amino acids, fluoro derivatives or any other substance that promotes the dispersion and compatibility of the filler in the composition.

Among the mineral fillers that may be used in the compositions according to the invention, mention may be made of talc, mica, silica, magnesium aluminium silicate, trimethyl siloxysilicate, kaolin, bentone, calcium carbonate, magnesium hydrogen carbonate, hydroxyapatite, boron nitride, hollow silica microspheres (Silica Beads from Maprecos), glass or ceramic microcapsules, silica-based fillers, for instance Aerosil 200 or Aerosil 300; Sunsphere H-33 and Sunsphere H-51 sold by Asahi Glass; Chemicelen sold by Asahi Chemical; composites of silica and of titanium dioxide, for instance the TSG series sold by Nippon Sheet Glass, perlite powders and fluorphlogopite, and mixtures thereof.

Among the organic fillers that may be used, mention may be made of polyamide powders (Nylon® Orgasol from Atochem), poly-β-alanine powders and polyethylene powders, polytetrafluoroethylene powders (Teflon), lauroyllysine, starch, tetrafluoroethylene polymer powders, hollow polymer microspheres, for example comprising an (alkyl) acrylate, such as Expancel® (Nobel Industrie), metal soaps derived from organic carboxylic acids containing from 8 to 22 carbon atoms and preferably from 12 to 18 carbon atoms, for example zinc stearate, magnesium stearate, lithium stearate, zinc laurate, magnesium myristate, Polypore® L200 (Chemdal Corporation), silicone resin microbeads (for example Tospearl® from Toshiba), polyurethane powders, in particular powders of crosslinked polyurethane comprising a copolymer, the said copolymer comprising trimethylol hexyl lactone, for instance the hexamethylene diisocyanate/trimethylol hexyl lactone polymer sold under the name Plastic Powder D-400® or Plastic Powder D-800® by the company Toshiki, carnauba microwaxes, such as the product sold under the name Micro Care 350® by the company Micro Powders, synthetic microwaxes, such as the product sold under the name MicroEase 114S® by the company Micro Powders, microwaxes formed from a mixture of carnauba wax and polyethylene wax, such as those sold Micro Care 300® and 310® by the company Micro Powders, microwaxes formed from a mixture of carnauba wax and of synthetic wax, such as the product sold under the name Micro Care 325® by the company Micro Powders, polyethylene microwaxes, such as those sold under the names Micropoly 200®, 220®, 220L® and 250S® by the company Micro Powders; fibres of synthetic or natural, mineral or organic origin. They may be short or long, individual or organized, for example braided, and hollow or solid. They may have any shape and may especially have a circular or polygonal (square, hexagonal or octagonal) cross section depending on the specific application envisaged. In particular, their ends are blunted and/or polished to prevent injury. The fibres have a length ranging from 1 µm to 10 mm, preferably from 0.1 mm to 5 mm and better still from 0.3 mm to 3 mm. Their cross section may be included in a circle with a diameter ranging from 2 nm to 500 µm, preferably ranging from 100 nm to 100 µm and better still from 1 µm to 50 µm. As fibres that can be used in the compositions according to the invention, mention may be made of non-rigid fibres such as polyamide (Nylon®) fibres or rigid fibres such as polyimideamide fibres, for instance those sold under the names Kermel® and Kermel Tech® by the company Rhodia or poly(p-phenyleneterephthalamide) (or aramid) fibres sold especially under the name Kevlar® by the company DuPont de Nemours, and mixtures thereof.

As representatives of such fillers preferably used in the context of the present invention, mention may be made especially of talc, starch, fluorphlogopite, clays such as magnesium aluminium silicate, or hollow polymer microspheres.

The fillers may be present in the composition in a content ranging from 1% to 40% by weight and preferably from 2% to 20% by weight relative to the total weight of the composition.

Colouring Agents

The coloring agent or dyestuff according to the invention is preferably chosen from pigments, nacres and reflective particles, and mixtures thereof.

According to one advantageous embodiment, the nacre(s) are present in a higher (total) weight content than the (total) content of pigment(s).

For example, the nacre(s) and the pigment(s) are present in the composition in a respective (total) content such that the weight ratio of the nacre(s) to the pigment(s) is between 12 and 1, better still between 11 and 4 and preferably between 10 and 6, and is approximately equal to 9.

Pigments

The term "pigments" should be understood as meaning white or coloured, mineral or organic particles of any shape, which are insoluble in the physiological medium, and which are intended to colour the composition.

The pigments may be white or coloured, and mineral and/or organic.

Among the mineral pigments that may be mentioned are titanium dioxide, optionally surface-treated, zirconium oxide or cerium oxide, and also zinc oxide, iron (black, yellow or red) oxide or chromium oxide, manganese violet, ultramarine blue, chromium hydrate and ferric blue, and metal powders, for instance aluminium powder and copper powder.

The organic pigments may be chosen from the materials below, and mixtures thereof:

cochineal carmine, organic pigments of azo dyes, anthraquinone dyes, indigoid dyes, xanthene dyes, pyrene dyes, quinoline dyes, triphenylmethane dyes and fluorane dyes.

Among the organic pigments, mention may be made especially of the D&C certified pigments known under the following names: D&C Blue No. 4, D&C Brown No. 1, D&C Green No. 5, D&C Green No. 6, D&C Orange No. 4, D&C Orange No. 5, D&C Orange No. 10, D&C Orange No. 11, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Violet No. 2, D&C Yellow No. 7, D&C Yellow No. 8, D&C Yellow No. 10, D&C Yellow No. 11, FD&C Blue No. 1, FD&C Green No. 3, FD&C Red No. 40, FD&C Yellow No. 5, FD&C Yellow No. 6.

The chemical materials corresponding to each of the organic dyestuffs mentioned previously are mentioned in the publication "International Cosmetic Ingredient Dictionary and Handbook", 1997 edition, pages 371 to 386 and 524 to 528, published by The Cosmetic, Toiletries and Fragrance Association, the content of which is incorporated into the present patent application by reference.

A composition according to the invention may comprise a content of pigments ranging from 0 to 30% by weight relative to the total weight of the composition, preferably ranging from 2% to 20% by weight and preferentially ranging from 4% to 10% by weight, relative to the total weight of the composition.

Nacres

The terms "nacres" should be understood as meaning coloured particles of any form, which may or may not be iridescent, especially produced by certain molluscs in their shell, or alternatively synthesized, and which have a colour effect via optical interference.

Examples of nacres that may be mentioned include nacreous pigments such as titanium mica coated with an iron oxide, mica coated with bismuth oxychloride, titanium mica coated with chromium oxide, and nacreous pigments based on bismuth oxychloride. They may also be mica particles at the surface of which are superposed at least two successive layers of metal oxides and/or of organic dyestuffs.

The nacres may more particularly have a yellow, pink, red, bronze, orange, brown, gold and/or coppery colour or glint.

As illustrations of nacres that may be introduced into the composition, mention may be made of the gold-coloured nacres sold especially by the company Engelhard under the name Brilliant gold 212G (Timica), Gold 222C (Cloisonne), Sparkle gold (Timica), Gold 4504 (Chromalite) and Monarch gold 233X (Cloisonne); the bronze nacres sold especially by the company Merck under the name Bronze fine (17384) (Colorona) and Bronze (17353) (Colorona) and by the company Engelhard under the name Super bronze (Cloisonne); the orange nacres sold especially by the company Engelhard under the name Orange 363C (Cloisonne) and Orange MCR 101 (Cosmica) and by the company Merck under the name Passion orange (Colorona) and Matte orange (17449) (Microna); the brown nacres sold especially by the company Engelhard under the name Nu-antique copper 340XB (Cloisonne) and Brown CL4509 (Chromalite); the nacres with a copper tint sold especially by the company Engelhard under the name Copper 340A (Timica); the nacres with a red tint sold especially by the company Merck under the name Sienna fine (17386) (Colorona); the nacres with a yellow tint sold especially by the company Engelhard under the name Yellow (4502) (Chromalite); the red nacres with a gold tint sold especially by the company Engelhard under the name Sunstone G012 (Gemtone); the pink nacres sold especially by the company Engelhard under the name Tan opale G005 (Gemtone); the black nacres with a gold tint sold especially by the company Engelhard under the name Nu antique bronze 240 AB (Timica), the blue nacres sold especially by the company Merck under the name Matte blue (17433) (Microna), the white nacres with a silvery tint sold especially by the company Merck under the name Xirona Silver, and the golden-green pink-orange nacres sold especially by the company Merck under the name Indian summer (Xirona), and mixtures thereof.

Still as examples of nacres, mention may also be made of particles comprising a borosilicate substrate coated with titanium oxide.

Particles having a glass substrate coated with titanium oxide are especially sold under the name Metashine MC1080RY by the company Toyal.

Finally, examples of nacres that may also be mentioned include polyethylene terephthalate flakes, especially those sold by the company Meadowbrook Inventions under the name Silver 1P 0.004X0.004 (silver flakes).

The compositions according to the invention preferably comprise a nacre content of greater than or equal to 30%, better still greater than or equal to 40% and even better still 50% by weight relative to the total weight of the composition. In particular, the said composition preferentially comprises a nacre content of between 30% and 70% by weight and preferably between 40% and 60% by weight relative to the total weight of the composition.

The compositions according to the invention preferably comprise from 50% to 98%, for example from 70% to 95% and better still from 80% to 92% by weight of nacres relative to the total weight of colouring agents. In particular, they advantageously comprise a content of greater than or equal to 85% by weight of nacres relative to the total weight of colouring agents.

The compositions according to the invention preferably comprise from 40% to 95%, for example from 50% to 90% and better still from 60% to 85% by weight of nacres relative to the total weight of the pulverulent phase. In particular, they advantageously comprise a content of greater than or equal to 70% by weight of nacres relative to the total weight of the pulverulent phase.

Reflective Particles

The term "reflective particles" denotes particles whose size, structure, especially the thickness of the layer(s) of which they are made and their physical and chemical nature, and surface state, allow them to reflect incident light. This reflection may, where appropriate, have an intensity sufficient to create at the surface of the composition or of the mixture, when it is applied to the support to be made up, points of overbrightness that are visible to the naked eye, i.e. more luminous points that contrast with their environment by appearing to sparkle.

The reflective particles may be selected so as not to significantly alter the colouration effect generated by the colouring agents with which they are combined, and more particularly so as to optimize this effect in terms of colour yield. They may more particularly have a yellow, pink, red, bronze, orange, brown, gold and/or coppery colour or tint.

These particles may have varied forms and may especially be in platelet or globular form, in particular in spherical form.

The reflective particles, whatever their form, may or may not have a multilayer structure and, in the case of a multilayer structure, may have, for example, at least one layer of uniform thickness, in particular of a reflective material.

When the reflective particles do not have a multilayer structure, they may be composed, for example, of metal oxides, especially titanium or iron oxides obtained synthetically.

When the reflective particles have a multilayer structure, they may comprise, for example, a natural or synthetic substrate, especially a synthetic substrate at least partially coated with at least one layer of a reflective material, especially of at least one metal or metallic material. The substrate may be made of one or more organic and/or inorganic materials.

More particularly, it may be chosen from glasses, ceramics, graphite, metal oxides, aluminas, silicas, silicates, especially aluminosilicates and borosilicates, and synthetic mica, and mixtures thereof, this list not being limiting.

The reflective material may comprise a layer of metal or of a metallic material.

Reflective particles are described especially in documents JP-A-09188830, JP-A-10158450, JP-A-10158541, JP-A-07258460 and JP-A-05017710.

Again as an example of reflective particles comprising a mineral substrate coated with a layer of metal, mention may also be made of particles comprising a silver-coated borosilicate substrate.

Particles with a silver-coated glass substrate, in the form of platelets, are sold under the name Microglass Metashine REFSX 2025 PS by the company Toyal. Particles with a glass substrate coated with nickel/chromium/molybdenum alloy are sold under the name Crystal Star GF 550 and GF 2525 by this same company.

Use may also be made of particles comprising a metallic substrate such as silver, aluminium, iron, chromium, nickel, molybdenum, gold, copper, zinc, tin, manganese, steel, bronze or titanium, said substrate being coated with at least one layer of at least one metal oxide such as titanium oxide, aluminium oxide, iron oxide, cerium oxide, chromium oxide or silicon oxides, and mixtures thereof.

Examples that may be mentioned include aluminium powder, bronze powder or copper powder coated with $SiO_2$ sold under the name Visionaire by the company Eckart.

Preferably, the pulverulent phase comprises at least one compound chosen from:
organic pigments such as, for example:
  the pigments certified D&C by the Food & Drug Administration as listed in the section "Color Additives—Batch Certified by the U.S. Food and Drug Administration" of the CTFA; mention may be made especially of Blue 1 and 4, Brown 1, Ext. Violet 2, Ext. Yellow 7, Green 3, 5, 6 and 8, Orange 4, 5, 10 and 11, Red 4, 6, 7, 17, 21, 22, 27, 28, 30, 36 and 40, Violet 2, Yellow 5, 6, 7, 8, 10 and 11,
mineral pigments such as:
  iron oxide, titanium oxide, zirconium oxide, cerium oxide, zinc oxide, iron oxide or chromium oxide,
  ferric blue, manganese violet, ultramarine blue, pink or violet, chromium hydrate, chromium hydroxide or bismuth oxychloride,
nacres such as, for example:
  mica coated with titanium oxide, mica coated with titanium oxide and iron oxide, and mica coated with an amino acid such as lauroyl lysine,
  polyethylene terephthalate flakes,
  sericite,
  and mixtures thereof,
reflective particles such as, for example:
  particles comprising a borosilicate substrate coated with a metallic layer.

Liquid Fatty Phase

A solid cosmetic composition according to the invention comprises at least one liquid fatty phase.

This fatty phase may advantageously serve as binder for the said pulverulent phase.

A liquid fatty phase preferably comprises at least one non-volatile oil.

The term "liquid" refers to a composition that is liquid at room temperature (25° C.) and atmospheric pressure (760 mmHg).

The term "oil" means a water-immiscible non-aqueous compound that is liquid at room temperature (25° C.) and at atmospheric pressure (760 mmHg).

The term "non-volatile oil" means an oil that remains on the skin or the keratin fibre at room temperature and pressure. More precisely, a non-volatile oil has an evaporation rate strictly less than 0.01 mg/cm²/min.

A solid composition according to the invention advantageously has a content of liquid fatty phase, and in particular of non-volatile oil(s), of greater than or equal to 15% by weight, in particular greater than or equal to 25% by weight, more particularly ranging from 25% to 50% by weight and better still from 30% to 40% by weight relative to the total weight of the composition.

A solid composition according to the invention preferably comprises at least one non-volatile hydrocarbon-based oil. Preferably, this non-volatile hydrocarbon-based oil comprises at least $C_{12}$-$C_{15}$ alkyl benzoates, alone or, preferably, mixed with an additional non-volatile hydrocarbon-based oil or preferably with a non-volatile silicone oil.

The content of $C_{12}$-$C_{15}$ alkyl benzoates in the said composition may range from 10% to 35% by weight, in particular from 15% to 30% by weight and better still from 20% to 25% by weight relative to the total weight of the composition.

According to one particular embodiment, the said composition has a total content of additional non-volatile hydrocarbon-based or silicone oil(s) of greater than or equal to 8% by weight relative to the total weight of the composition and better still 10% by weight relative to the total weight of the composition. This total content of additional non-volatile hydrocarbon-based or silicone oil(s) is more generally advantageously between 2% and 20% by weight relative to the total weight of the composition.

Hydrocarbon-Based Non-Volatile Oil

A liquid fatty phase preferably comprises at least one non-volatile hydrocarbon-based oil chosen from the $C_{12}$-$C_{15}$ alkyl benzoates of formula (A) below:

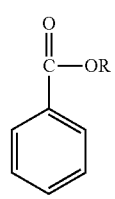

(A)

in which formula (A) R is a $C_{12}$-$C_{15}$ alkyl group.

This non-volatile oil is derived from the esterification of benzoic acid with one or more $C_{12}$-$C_{15}$ alcohols.

The content of $C_{12}$-$C_{15}$ alkyl benzoates in the said composition may range from 10% to 35% by weight, in particular from 15% to 30% by weight and better still from 20% to 25% by weight relative to the total weight of the composition.

The $C_{12}$-$C_{15}$ alkyl benzoate(s) may be provided in a composition according to the invention, alone or, preferably, as a mixture with one or more additional non-volatile hydrocarbon-based or silicone oils, and mixtures thereof, more preferentially with at least one non-volatile silicone oil.

A composition according to the invention may also comprise one or more additional non-volatile hydrocarbon-based oils.

Additional non-volatile hydrocarbon-based oils that may especially be mentioned include:

hydrocarbon-based oils of plant origin, such as phytostearyl esters, such as phytostearyl oleate, phytostearyl isostearate and lauroyl/octyldodecyl/phytostearyl glutamate; triglycerides formed from fatty acid esters of glycerol, in particular whose fatty acids may have chain lengths ranging from $C_{18}$ to $C_{36}$, these oils possibly being linear or branched, and saturated or unsaturated; these oils may especially be heptanoic or octanoic triglycerides, shea oil, alfalfa oil, poppy oil, pumpkin oil, millet oil, barley oil, quinoa oil, rye oil, candlenut oil, passionflower oil, shea butter oil, aloe oil, sweet almond oil, peach stone oil, groundnut oil, argan oil, avocado oil, baobab oil, borage oil, broccoli oil, calendula oil, camellina oil, carrot oil, safflower oil, hemp oil, rapeseed oil, cottonseed oil, coconut oil, marrow seed oil, wheatgerm oil, jojoba oil, lily oil, macadamia oil, corn oil, meadowfoam oil, St-John's wort oil, monoi oil, hazelnut oil, apricot kernel oil, walnut oil, olive oil, evening primrose oil, palm oil, blackcurrant pip oil, kiwi seed oil, grape seed oil, pistachio oil, pumpkin oil, quinoa oil, musk rose oil, sesame oil, soybean oil, sunflower oil, castor oil and watermelon oil, and mixtures thereof, or alternatively caprylic/capric acid triglycerides, such as those sold by the company Stéarineries Dubois or those sold under the names Miglyol 810®, 812® and 818® by the company Dynamit Nobel;

synthetic ethers containing from 10 to 40 carbon atoms;

synthetic esters, for instance the oils of formula $R_1COOR_2$, other than a $C_{12}$-$C_{15}$ alkyl benzoate, in which $R_1$ represents at least one linear or branched fatty acid residue comprising from 1 to 40 carbon atoms and $R_2$ represents a hydrocarbon-based chain, which is especially branched, containing from 1 to 40 carbon atoms, on condition that $R_1+R_2$ is greater than or equal to 10. The esters may be chosen especially from fatty acid esters of alcohols, for instance cetostearyl octanoate, isopropyl alcohol esters, such as isopropyl myristate, isopropyl palmitate, ethyl palmitate, 2-ethylhexyl palmitate, isopropyl stearate, isopropyl isostearate, isostearyl isostearate, octyl stearate, hydroxylated esters, for instance isostearyl lactate, octyl hydroxystearate, diisopropyl adipate, heptanoates, and especially isostearyl heptanoate, alcohol or polyalcohol octanoates, decanoates or ricinoleates, for instance propylene glycol dioctanoate, cetyl octanoate, tridecyl octanoate, 2-ethylhexyl 4-diheptanoate, 2-ethylhexyl palmitate, alkyl benzoates, polyethylene glycol diheptanoate, propylene glycol 2-diethylhexanoate, and mixtures thereof, hexyl laurate, neopentanoic acid esters, for instance isodecyl neopentanoate, isotridecyl neopentanoate, isostearyl neopentanoate, octyldodecyl neopentanoate, isononanoic acid esters, for instance isononyl isononanoate, isotridecyl isononanoate, octyl isononanoate, hydroxylated esters, for instance isostearyl lactate and diisostearyl malate;

polyol esters and pentaerythritol esters, for instance dipentaerythrityl tetrahydroxystearate/tetraisostearate;

esters of diol dimers and of diacid dimers;

copolymers of diol dimer and of diacid dimer and esters thereof, such as dilinoleyl diol dimer/dilinoleic dimer copolymers, and esters thereof;

copolymers of polyols and of diacid dimers, and esters thereof;

fatty alcohols that are liquid at room temperature, with a branched and/or unsaturated carbon-based chain containing from 12 to 26 carbon atoms, for instance 2-octyldodecanol, isostearyl alcohol, oleyl alcohol, 2-hexyldecanol, 2-butyloctanol and 2-undecylpentadecanol;

$C_{12}$-$C_{22}$ higher fatty acids, such as oleic acid, linoleic acid and linolenic acid, and mixtures thereof;

dialkyl carbonates, the two alkyl chains possibly being identical or different, such as dicaprylyl carbonate;

oils with a molar mass of between about 400 and about 10 000 g/mol, in particular about 650 to about 10 000 g/mol, in particular from about 750 to about 7500 g/mol and more particularly ranging from about 1000 to about 5000 g/mol; mention may be made especially, alone or as a mixture, of (i) lipophilic polymers such as polybutylenes, polyisobutylenes, for example hydrogenated, polydecenes and hydrogenated polydecenes, vinylpyrrolidone copolymers, such as the vinylpyrrolidone/1-hexadecene copolymer, and polyvinylpyrrolidone (PVP) copolymers, such as the copolymers of a $C_2$-$C_{30}$ alkene, such as $C_3$-$C_{22}$, and combinations thereof; (ii) linear fatty acid esters containing a total carbon number ranging from 35 to 70, for instance pentaerythrityl tetrapelargonate; (iii) hydroxylated esters such as polyglyceryl-2-triisostearate; (iv) aromatic esters such as tridecyl trimellitate; (v) esters of fatty alcohols or of branched $C_{24}$-$C_{28}$ fatty acids, such as those described in U.S. Pat. No. 6,491,927 and pentaerythritol esters, and especially triisoarachidyl citrate, pentaerythrityl tetraisononanoate, glyceryl triisostearate, glyceryl 2-tridecyltetradecanoate, pentaerythrityl tetraisostearate, poly(2-glyceryl)tetraisostearate or pentaerythrityl 2-tetradecyltetradecanoate; (vi) diol dimer esters and polyesters, such as esters of diol dimer and of fatty acid, and esters of diol dimer and of diacid.

According to one particular embodiment, a composition according to the invention is free of additional non-volatile hydrocarbon-based oil(s).

Non-Volatile Silicone Oils

According to one preferred embodiment of the invention, the compositions according to the invention comprise at least one non-volatile silicone oil.

Preferentially, a composition according to the invention comprises at least one volatile hydrocarbon-based oil, advantageously chosen from $C_{12}$-$C_{15}$ alkyl benzoates, as a mixture with one or more non-volatile silicone oil(s).

The non-volatile silicone oil that may be used in the invention may be chosen from silicone oils with a viscosity at 25° C. of greater than or equal to 9 centistokes (cSt) ($9\times10^{-6}$ m$^2$/s) and less than 800 000 cSt, preferably between 50 and 600 000 cSt and preferably between 100 and 500 000 cSt. The viscosity of this silicone may be measured according to standard ASTM D-445.

Among these silicone oils, two types of oil may be distinguished, according to whether or not they contain phenyl.

Representative examples of these non-volatile linear silicone oils that may be mentioned include polydimethylsiloxanes; alkyl dimethicones; vinyl methyl methicones; and also silicones modified with optionally fluorinated aliphatic groups, or with functional groups such as hydroxyl, thiol and/or amine groups.

Thus, non-phenyl non-volatile silicone oils that may be mentioned include:

PDMSs comprising alkyl or alkoxy groups, which are pendent and/or at the end of the silicone chain, these groups each containing from 2 to 24 carbon atoms, PDMSs comprising aliphatic groups, or functional groups such as hydroxyl, thiol and/or amine groups, polyalkylmethylsiloxanes optionally substituted with a fluorinated group, such as polymethyltrifluoropropyldimethylsiloxanes, polyalkylmethylsiloxanes substituted with functional groups such as hydroxyl, thiol and/or amine groups, polysiloxanes modified with fatty acids, fatty alcohols or polyoxyalkylenes, and mixtures thereof.

According to one particular embodiment, a composition according to the invention contains at least one non-phenyl linear silicone oil.

The non-phenyl linear silicone oil may be chosen especially from the silicones of formula:

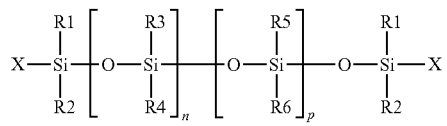

in which:

$R_1$, $R_2$, $R_5$ and $R_6$ are, together or separately, an alkyl radical containing 1 to 6 carbon atoms, $R_3$ and $R_4$ are, together or separately, an alkyl radical containing from 1 to 6 carbon atoms, a vinyl radical, an amine radical or a hydroxyl radical, X is an alkyl radical containing from 1 to 6 carbon atoms, a hydroxyl radical or an amine radical, n and p are integers chosen so as to have a fluid compound.

As non-volatile silicone oils that may be used according to the invention, mention may be made of those for which:

the substituents $R_1$ to $R_6$ and X represent a methyl group, and p and n are such that the viscosity is 500 000 cSt, such as the product sold under the name SE30 by the company General Electric, the product sold under the name AK 500000 by the company Wacker, the product sold under the name Mirasil DM 500 000 by the company Bluestar, and the product sold under the name Dow Corning 200 Fluid 500 000 cSt by the company Dow Corning, the substituents $R_1$ to $R_6$ and X represent a methyl group, and p and n are such that the viscosity is 60 000 cSt, such as the product sold under the name Dow Corning 200 Fluid 60000 CS by the company Dow Corning, and the product sold under the name Wacker Belsil DM 60 000 by the company Wacker, the substituents $R_1$ to $R_6$ and X represent a methyl group, and p and n are such that the viscosity is 350 cSt, such as the product sold under the name Dow Corning 200 Fluid 350 CS by the company Dow Corning, the substituents $R_1$ to $R_6$ represent a methyl group, the group X represents a hydroxyl group, and n and p are such that the viscosity is 700 cSt, such as the product sold under the name Baysilone Fluid T0.7 by the company Momentive.

According to one preferred embodiment variant, a composition according to the invention contains at least one phenyl silicone oil.

Representative examples of these non-volatile phenyl silicone oils that may be mentioned include:

the phenyl silicone oils corresponding to the following formula:

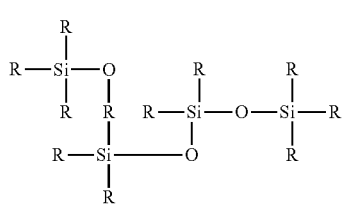

in which formula (I) the groups R represent, independently of each other, a methyl or a phenyl, with the proviso that at least one group R represents a phenyl. Preferably, in this formula, the phenyl silicone oil comprises at least three phenyl groups, for example at least four, at least five or at least six.

the phenyl silicone oils corresponding to the following formula:

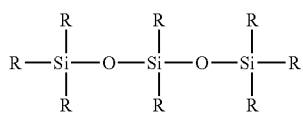

in which formula (II) the groups R represent, independently of each other, a methyl or a phenyl, with the proviso that at least one group R represents a phenyl. Preferably, in this formula, the said organopolysiloxane comprises at least three phenyl groups, for example at least four or at least five. Mixtures of the phenyl organopolysiloxanes described previously may be used. Examples that may be mentioned include mixtures of triphenyl, tetraphenyl or pentaphenyl organopolysiloxanes.

the phenyl silicone oils corresponding to the following formula:

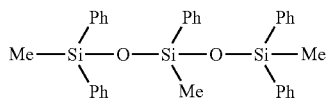

in which formula (III) Me represents methyl, Ph represents phenyl. Such a phenyl silicone is especially manufactured by Dow Corning under the reference PH-1555 HRI or Dow Corning 555 Cosmetic Fluid (chemical name: 1,3,5-trimethyl-1,1,3,5,5-pentaphenyl trisiloxane; INCI name: trimethyl pentaphenyl trisiloxane). The reference Dow Corning 554 Cosmetic Fluid may also be used.

the phenyl silicone oils corresponding to the following formula:

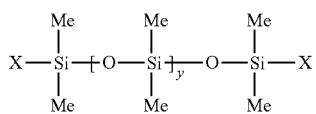

in which formula (IV) Me represents methyl, y is between 1 and 1000 and X represents —$CH_2$—$CH(CH_3)$(Ph).

the phenyl silicone oils corresponding to formula (V) below:

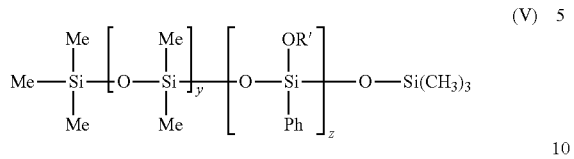
(V)

in which formula (V) Me is methyl and Ph is phenyl, OR' represents a group —OSiMe$_3$ and y is 0 or ranges between 1 and 1000, and z ranges between 1 and 1000, such that compound (V) is a non-volatile oil.

According to a first embodiment, y ranges between 1 and 1000. Use may be made, for example, of trimethyl siloxy-phenyl dimethicone, sold especially under the reference Belsil PDM 1000 sold by the company Wacker.

According to a second embodiment, y is equal to 0. Use may be made, for example, of phenyl trimethylsiloxy trisiloxane, sold especially under the reference Dow Corning 556 Cosmetic Grade Fluid, the phenyl silicone oils corresponding to formula (VI) below, and mixtures thereof:

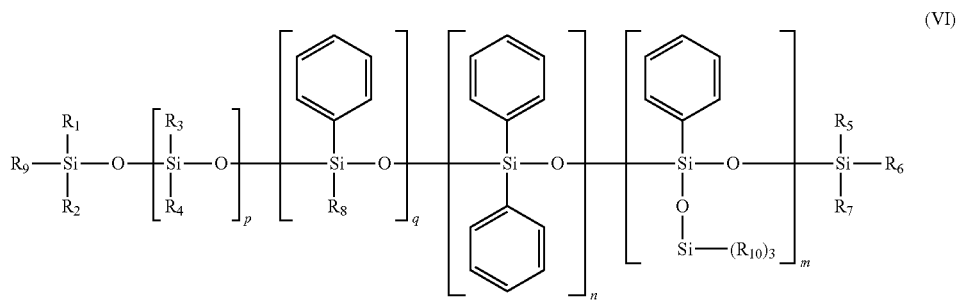
(VI)

in which formula (VI):

$R_1$ to $R_{10}$, independently of each other, are saturated or unsaturated, linear, cyclic or branched $C_1$-$C_{30}$ hydrocarbon-based radicals, m, n, p and q are, independently of each other, integers between 0 and 900, with the proviso that the sum m+n+q is other than 0.

Preferably, the sum m+n+q is between 1 and 100. Preferably, the sum m+n+p+q is between 1 and 900 and better still between 1 and 800. Preferably, q is equal to 0.

the phenyl silicone oils corresponding to formula (VII) below, and mixtures thereof:

in which formula (VII):

$R_1$ to $R_6$, independently of each other, are saturated or unsaturated, linear, cyclic or branched $C_1$-$C_{30}$ hydrocarbon-based radicals, m, n and p are, independently of each other, integers between 0 and 100, with the proviso that the sum n+m is between 1 and 100.

Preferably, $R_1$ to $R_6$, independently of each other, represent a saturated, linear or branched $C_1$-$C_{30}$ and especially $C_1$-$C_{12}$ hydrocarbon-based radical and in particular a methyl, ethyl, propyl or butyl radical.

$R_1$ to $R_6$ may especially be identical, and in addition may be a methyl radical.

Preferably, m=1 or 2 or 3, and/or n=0 and/or p=0 or 1 may apply, in formula (VII).

the phenyl silicone oils corresponding to formula (VIII), and mixtures thereof:

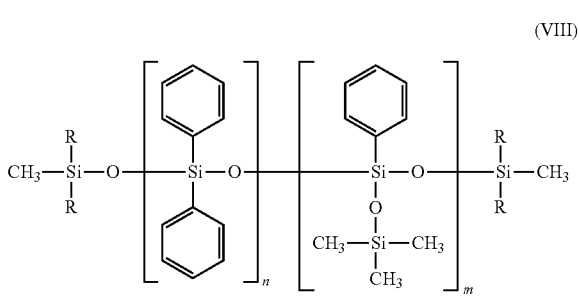
(VIII)

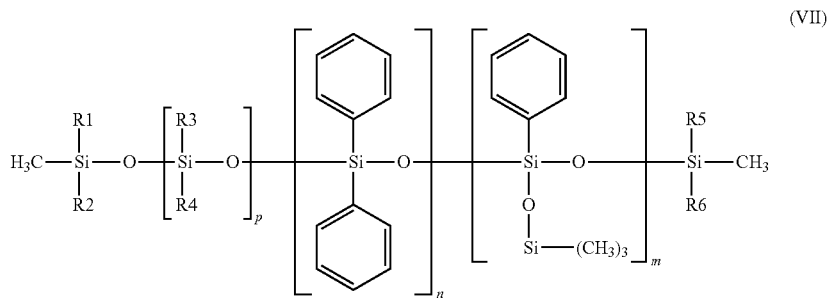
(VII)

in which formula (VIII):

R is a $C_1$-$C_{30}$ alkyl radical, an aryl radical or an aralkyl radical, n is an integer ranging from 0 to 100, and m is an integer ranging from 0 to 100, with the proviso that the sum n+m ranges from 1 to 100.

In particular, the radicals R of formula (VIII) and $R_1$ to $R_{10}$ defined previously may each represent a linear or branched, saturated or unsaturated alkyl radical, especially of $C_2$-$C_{20}$, in particular $C_3$-$C_{16}$ and more particularly $C_4$-$C_{10}$, or a monocyclic or polycyclic $C_6$-$C_{14}$ and especially $C_{10}$-$C_{13}$ aryl radical, or an aralkyl radical whose aryl and alkyl residues are as defined previously.

Preferably, R of formula (VIII) and $R_1$ to $R_{10}$ may each represent a methyl, ethyl, propyl, isopropyl, decyl, dodecyl or octadecyl radical, or alternatively a phenyl, tolyl, benzyl or phenethyl radical.

According to one embodiment, a phenyl silicone oil of formula (VIII) with a viscosity at 25° C. of between 5 and 1500 mm$^2$/s (i.e. 5 to 1500 cSt), and preferably with a viscosity of between 5 and 1000 mm$^2$/s (i.e. 5 to 1000 cSt) may be used.

As phenyl silicone oils of formula (VIII), it is especially possible to use phenyl trimethicones such as DC556 from Dow Corning (22.5 cSt), the oil Silbione 70663V30 from Rhône-Poulenc (28 cSt) or diphenyl dimethicones such as Belsil oils, especially Belsil PDM1000 (1000 cSt), Belsil PDM 200 (200 cSt) and Belsil PDM 20 (20 cSt) from Wacker. The values in parentheses represent the viscosities at 25° C.

the phenyl silicone oils corresponding to the following formula, and mixtures thereof:

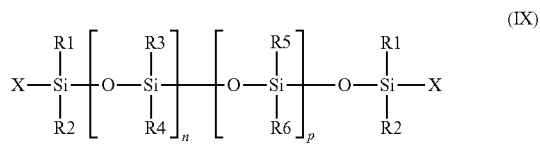

(IX)

in which formula (IX):

$R_1$, $R_2$, $R_5$ and $R_6$ are, together or separately, an alkyl radical containing 1 to 6 carbon atoms, $R_3$ and $R_4$ are, together or separately, an alkyl radical containing from 1 to 6 carbon atoms or an aryl radical, X is an alkyl radical containing from 1 to 6 carbon atoms, a hydroxyl radical or a vinyl radical, n and p being chosen so as to give the oil a weight-average molecular mass of less than 200 000 g/mol, preferably less than 150 000 g/mol and more preferably less than 100 000 g/mol.

The phenyl silicones that are most particularly suitable for use in the invention are those corresponding to formulae (II) and especially to formulae (III), (V) and (VIII) hereinabove.

More particularly, the phenyl silicones are chosen from phenyl trimethicones, phenyl dimethicones, phenyl-trimethylsiloxydiphenylsiloxanes, diphenyl dimethicones, diphenylmethyldiphenyltrisiloxanes and 2-phenylethyl trimethylsiloxysilicates, and mixtures thereof.

Preferably, the weight-average molecular weight of the non-volatile phenyl silicone oil according to the invention ranges from 500 to 10 000 g/mol.

It should be noted that, among the silicone compounds according to the invention, phenyl silicone oils prove to be particularly advantageous.

Volatile Oil

The liquid fatty phase may optionally comprise at least one volatile oil.

The term "volatile oil" means an oil (or non-aqueous medium) that can evaporate on contact with the skin in less than one hour, at room temperature and atmospheric pressure. The volatile oil is a cosmetic volatile oil, which is liquid at room temperature. More specifically, a volatile oil has an evaporation rate of between 0.01 and 200 mg/cm$^2$/min, limits included.

To measure this evaporation rate, 15 g of oil or of oil mixture to be tested are placed in a crystallizing dish 7 cm in diameter, which is placed on a balance in a large chamber of about 0.3 m$^3$ that is temperature-regulated, at a temperature of 25° C., and hygrometry-regulated, at a relative humidity of 50%. The liquid is allowed to evaporate freely, without stirring it, while providing ventilation by means of a fan (Papst-Motoren, reference 8550 N, rotating at 2700 rpm) placed in a vertical position above the crystallizing dish containing said oil or said mixture, the blades being directed towards the crystallizing dish, 20 cm away from the bottom of the crystallizing dish. The mass of oil remaining in the crystallizing dish is measured at regular intervals. The evaporation rates are expressed in mg of oil evaporated per unit of area (cm$^2$) and per unit of time (minutes).

This volatile oil may be a hydrocarbon-based oil, silicone oil or fluoro oil. It is preferably a hydrocarbon-based oil.

The term "hydrocarbon-based oil" means an oil mainly containing hydrogen and carbon atoms.

The term "silicone oil" means an oil containing at least one silicon atom, and especially containing Si—O groups. According to one embodiment, the said composition comprises less than 10% by weight of non-volatile silicone oil(s), relative to the total weight of the composition, better still less than 5% by weight, or even is free of silicone oil.

The term "fluoro oil" means an oil comprising at least one fluorine atom.

The oils may optionally comprise oxygen, nitrogen, sulfur and/or phosphorus atoms, for example in the form of hydroxyl or acid radicals.

The volatile oils may be chosen from hydrocarbon-based oils containing from 8 to 16 carbon atoms, and especially $C_8$-$C_{16}$ branched alkanes (also known as isoparaffins), for instance isododecane, isodecane and isohexadecane.

The volatile hydrocarbon-based oil may also be a linear volatile alkane containing 7 to 17 carbon atoms, in particular 9 to 15 carbon atoms and more particularly 11 to 13 carbon atoms. Mention may be made especially of n-nonadecane, n-decane, n-undecane, n-dodecane, n-tridecane, n-tetradecane, n-pentadecane and n-hexadecane, and mixtures thereof.

Preferably, the composition is free of volatile oil. Such an absence of volatile oil makes it possible, where appropriate, to dispense with a perfectly leaktight conditioning assembly for the said composition.

Amorphous Hydrocarbon-Based Block Copolymer

The composition according to the invention comprises at least one amorphous hydrocarbon-based block copolymer, preferably a block copolymer that is soluble or dispersible in the liquid fatty phase. Such a copolymer may thus serve as gelling agent for this fatty phase.

The hydrocarbon-based block copolymer may especially be a diblock, triblock, multiblock, radial or star copolymer, or mixtures thereof.

Such hydrocarbon-based block copolymers are described in patent application US-A-2002/005 562 and in U.S. Pat. No. 5,221,534.

The copolymer may contain at least one block whose glass transition temperature is preferably less than 20° C., preferably less than or equal to 0° C., preferably less than or equal to −20° C. and more preferably less than or equal to −40° C. The glass transition temperature of the said block may be between −150° C. and 20° C. and especially between 100° C. and 0° C.

The hydrocarbon-based block copolymer present in the composition according to the invention is preferably an amorphous copolymer formed by polymerization of an olefin. The olefin may especially be an elastomeric ethylenically unsaturated monomer.

Examples of olefins that may be mentioned include ethylenic carbide monomers, especially containing one or two ethylenic unsaturations and containing from 2 to 5 carbon atoms, such as ethylene, propylene, butadiene, isoprene or pentadiene.

Advantageously, the hydrocarbon-based block copolymer is an amorphous block copolymer of styrene and of an olefin.

Block copolymers comprising at least one styrene block and at least one block comprising units chosen from butadiene, ethylene, propylene, butylene and isoprene or a mixture thereof are especially preferred.

According to one preferred embodiment, the hydrocarbon-based block copolymer is hydrogenated to reduce the residual ethylenic unsaturations after the polymerization of the monomers.

In particular, the hydrocarbon-based block copolymer is an optionally hydrogenated copolymer, containing styrene blocks and ethylene/$C_3$-$C_4$ alkylene blocks.

Diblock copolymers, which are preferably hydrogenated, that may be mentioned include styrene-ethylene/propylene copolymers, styrene-ethylene/butadiene copolymers and styrene-ethylene/butylene copolymers. Diblock polymers are especially sold under the name Kraton® G1701E by the company Kraton Polymers.

Triblock copolymers, which are preferably hydrogenated, that may be mentioned include styrene-ethylene/propylene-styrene copolymers, styrene-ethylene/butadiene-styrene copolymers, styrene-ethylene/butylene-styrene copolymers, styrene-isoprene-styrene copolymers and styrene-butadiene-styrene copolymers. Triblock polymers are especially sold under the names Kraton® G1650, Kraton® G1652, Kraton® D1101, Kraton® D1102 and Kraton® D1160 by the company Kraton Polymers.

According to one embodiment of the present invention, the hydrocarbon-based block copolymer is a styrene-ethylene/butylene-styrene triblock copolymer.

According to one preferred embodiment of the invention, it is especially possible to use a mixture of a styrene-butylene/ethylene-styrene triblock copolymer and of a styrene-ethylene/butylene diblock copolymer, especially the products sold under the name Kraton® G1657M by the company Kraton Polymers.

Preferably, a composition according to the invention comprises a content inclusively between 0.5% and 5% by weight and better still from 1.5% to 4% by weight of hydrocarbon-based block copolymer(s) relative to the total weight of the composition. The composition advantageously has a content of hydrocarbon-based block copolymer of greater than or equal to 1% by weight relative to the total weight of the composition.

Preferably, the amorphous hydrocarbon-based block copolymer(s) and the non-volatile hydrocarbon-based oil chosen from $C_{12}$-$C_{15}$ alkyl benzoates are present in the composition in a respective total content such that the weight ratio of the amorphous hydrocarbon-based block copolymer to the said $C_{12}$-$C_{15}$ alkyl benzoate(s) is inclusively between 0.06 and 0.3 and better still between 0.08 and 0.2.

Aqueous Phase

The composition according to the invention may comprise an aqueous phase.

This aqueous phase, when present, is used in an amount that is compatible with the pulverulent galenical form required according to the invention.

The aqueous phase may be a demineralized water or alternatively a floral water such as cornflower water and/or a mineral water such as Vittel water, Lucas water or La Roche Posay water and/or a spring water.

The aqueous phase may also comprise a polyol that is miscible with water at room temperature (25° C.) chosen especially from polyols especially containing from 2 to 20 carbon atoms, preferably containing from 2 to 10 carbon atoms and preferentially containing from 2 to 6 carbon atoms, such as glycerol, propylene glycol, butylene glycol, pentylene glycol, hexylene glycol, dipropylene glycol or diethylene glycol; glycol ethers (especially containing from 3 to 16 carbon atoms) such as mono-, di- or tripropylene glycol ($C_1$-$C_4$)alkyl ethers, mono-, di- or triethylene glycol ($C_1$-$C_4$)alkyl ethers; and mixtures thereof.

The composition according to the invention may comprise a polyol that is miscible with water at room temperature. Such polyols may promote the moisturization of the surface of the skin on which the composition is applied.

In addition, the composition according to the invention may comprise a monoalcohol containing from 2 to 6 carbon atoms, such as ethanol or isopropanol.

A composition according to the invention advantageously comprises less than 5% by weight of aqueous phase, and in particular of water, relative to the total weight of the composition. Preferentially, a composition according to the invention is free of aqueous phase, and in particular free of water.

Adjuvants

The composition may comprise other ingredients (adjuvants) usually used in cosmetics, such as preserving agents, cosmetic active agents, moisturizers, UV-screening agents, thickeners and fragrances.

Needless to say, a person skilled in the art will take care to select the optional adjuvant(s) added to the composition according to the invention such that the advantageous properties intrinsically associated with the composition in accordance with the invention are not, or are not substantially, adversely affected by the envisaged addition.

Assembly

According to another aspect, the invention also relates to a cosmetic assembly comprising:

i) a container delimiting one or more compartment(s), the said container being closed by a closing member and optionally not being leaktight; and ii) a makeup and/or care composition in accordance with the invention placed inside the said compartment(s).

The container may be, for example, in the form of a jar or a box.

The closing member may be in the form of a lid comprising a cap mounted so as to be able to move by translation or by pivoting relative to the container housing the said makeup and/or care composition(s).

EXAMPLE

A solid cosmetic composition, in the form of a compact powder or an eyeshadow, according to the invention was prepared as followed and then tested especially from the point of view of the impact strength and according to various cosmetic evaluation criteria.

| Phases | Compounds | % content |
|---|---|---|
| 1 | Pigments (iron oxides) | 6 |
|  | Nacres (coated mica) | 54 |
|  | Powder of hexamethylene/trimethylol hexyl lactone copolymer containing silica (Plastic Powder D 400) | 2 |
| 2 | Styrene-ethylene/butylene-styrene block copolymer (Kraton G1657M) | 2 |
|  | C12/C15 alkyl benzoate (Tegosoft TN from Evonik Goldschmidt) | 24 |
|  | Phenyl trimethicone (DC556 from Dow Corning) | 11 |
| 3 | Caprylyl glycol (Dermosoft Octiol® from Dr. Straetmans) | 1 |

The procedure below was used to prepare the compositions according to the invention.

1—Preparation of Phase 1:

The compounds of phase 1 (except for the nacres) are weighed out and then dispersed in a Novamix 1 L mixer-disperser for 3 minutes 30 seconds with paddle stirring at 3000 rpm and decaking at 2700 rpm. The nacres are then introduced into the mixer and dispersed for 3 minutes with paddles stirring at 3000 rpm.

2—Preparation of Phases 2 and 3:

The compounds of phase 2 are weighed out in a heating pan and then heated to 95° C., and homogenization is performed using a deflocculator (Turbotest 33/300 PH—Rayneri, VMI Group). Once the mixture is homogeneous, it is cooled to 55° C. for the introduction of the compound of phase 3.

3—Finalization of the Formulation:

Phases 2 and 3 are introduced into phase 1 in a Kenwood Chef KM010 mixer with minimum stirring over a few seconds, and the mixture is then homogenized for about 2 minutes. The preparation obtained is then pressed in a crucible.

Measurement of the Impact Strength

Measurement Principle

The machine used to perform such a measurement, known as a Package Drop-Test machine sold by the company Co Pack (Italy), makes it possible to perform drop tests on the solid compositions in compact powder form to measure their impact strength. The drop height is 30 cm. By means of a small ruler, the size of the support that holds the compact is set (according to the size of the crucible) and the compact is then dropped by means of compressed air that actuates the aperture of the support.

This machine replaces the manual drop tests performed previously by the formulator using a 30 cm ruler. In this new manner, they are repeatable and thus more reliable.

These drop tests are also included in the study of the stability of the compacts prepared.

Results:

An eyeshadow (ES) obtained via a conventional pressing process during which the pulverulent phase is mixed with a substantial fatty phase, for example present at 40% by weight relative to the total weight of the composition, does not withstand a drop. By means of the various tests performed on the nacreous tints according to the invention, having a similar fatty-phase content, it was observed that the pressed powders according to the invention withstand a number of drops strictly greater than 1, for example between 2 and 5.

This improvement in the impact strength is explained according to the inventors by the particular structuring of the fatty phase with the block copolymer and of the solid composition according to the invention with the particular non-volatile hydrocarbon-based oil, which makes it possible to obtain a pressed powder that is more resistant than a pressed powder obtained via the conventional processes lacking such compounds.

Evaluation of the Composition:

An evaluation protocol was performed on a panel of 65 experienced persons, and the result concerning the softness to the touch, the application (amount taken up, ease of application, adherence on application), the texture, the makeup result (uniformity, powdery effect, coverage, colour effect), the comfort throughout the day, the wear properties and the ease of removal of a composition according to the invention was evaluated by the same persons.

Results

In general, more than 85% of the panel said that they were satisfactory regarding these criteria considered alone or independently, the makeup result and the wear properties being the most satisfactory criteria.

The results obtained with the applied composition according to the invention show that the wear properties of the ES according to the invention are very good. Specifically, after 7 hours of application, during which the panellists are not subjected to any stress, 80% to 100% of the product remains on the eyelid after this period.

It is understood that, in the context of the present invention, the weight percentages given for a compound or a family of compounds are always expressed as weight of solids of the compound in question.

Throughout the application, the term "comprises one" or "includes one" should be understood as meaning "comprising at least one" or "including at least one", unless otherwise specified.

The invention claimed is:

1. A solid cosmetic composition consisting of, in a physiologically acceptable medium:
   a pulverulent phase in an amount of greater than or equal to 35% by weight relative to a total weight of the solid cosmetic composition,
   a liquid fatty phase comprising at least one non-volatile oil, wherein the at least one non-volatile oil is present in an amount of greater than or equal to 15% by weight relative to the total weight of the solid cosmetic composition,
   optionally an aqueous phase,
   an amorphous hydrocarbon-based block copolymer, and
   optionally at least one adjuvant selected from the group consisting of preserving agents, cosmetic active agents, moisturizers, UV-screening agents, thickeners, fragrances, and mixtures thereof,
   wherein the solid cosmetic composition is in a form of a compact powder,
   wherein the pulverulent phase comprises at least one nacre in an amount of greater than or equal to 30% by weight relative to the total weight of the solid cosmetic composition, and
   wherein the pulverulent phase comprises from 40% to 95% by weight of nacre(s) relative to the total weight of the pulverulent phase.

2. The solid cosmetic composition according to claim 1, wherein the solid cosmetic composition contains the pulverulent phase in an amount of greater than or equal to 50% by weight relative to the total weight of the solid cosmetic composition.

3. The solid cosmetic composition according to claim 1, wherein the solid cosmetic composition contains the at least one non-volatile oil in an amount of greater than or equal to 25% by weight relative to the total weight of the solid cosmetic composition.

4. The solid cosmetic composition according to claim 1, wherein the at least one non-volatile oil is a $C_{12}$-$C_{15}$ alkyl benzoate.

5. The solid cosmetic composition according to claim 1, wherein the at least one non-volatile oil is a linear non-volatile silicone oil and/or a phenylated non-volatile silicone oil.

6. The solid cosmetic composition according to claim 1, wherein the solid cosmetic composition contains the amorphous hydrocarbon-based block copolymer in an amount of greater than or equal to 1% by weight relative to the total weight of the solid cosmetic composition.

7. The solid cosmetic composition according to claim 1, wherein the non-volatile oil is a $C_{12}$-$C_{15}$ alkyl benzoate, and
the amorphous hydrocarbon-based block copolymer(s) and the $C_{12}$-$C_{15}$ alkyl benzoate are present in a respective total content such that a weight ratio of the amorphous hydrocarbon-based block copolymer to the $C_{12}$-$C_{15}$ alkyl benzoate is between 0.06 and 0.3.

8. The solid cosmetic composition according to claim 1, wherein the solid cosmetic composition is selected from the group consisting of an eyeshadow, a blusher and a powder with a healthy-complexion effect.

9. A process for coating eyelids with the solid cosmetic composition according to claim 1, the process comprising:
applying the solid cosmetic composition to the eyelids.

10. The solid cosmetic composition according to claim 1, wherein the solid cosmetic composition is in a form of pressed powder.

11. The solid cosmetic composition according to claim 1, wherein the solid cosmetic composition contains the at least one non-volatile oil in an amount of from 25% to 50% by weight relative to the total weight of the solid cosmetic composition.

12. The solid cosmetic composition according to claim 1, wherein the amorphous hydrocarbon-based block copolymer is hydrogenated.

13. The solid cosmetic composition according to claim 1, which contains 0.5% to 5% by weight of the hydrocarbon-based block copolymers.

14. The solid cosmetic composition according to claim 1, which contains 1.5% to 4% by weight of the hydrocarbon-based block copolymers.

15. A method of preparing the solid cosmetic composition according to claim 1, comprising combining the pulverulent phase, liquid fatty phase and amorphous hydrocarbon-based block copolymer in a physiologically acceptable medium.

16. The solid cosmetic composition according to claim 1, wherein the nacre is at least one member selected from the group consisting of titanium mica coated with an iron oxide, mica coated with bismuth oxychloride, titanium mica coated with chromium oxide, and nacreous pigments based on bismuth oxychloride, mica particles at the surface of which are superposed at least two successive layers of metal oxides, and mica particles at the surface of which are superposed at least two successive layers of organic dyestuffs.

17. The solid cosmetic composition according to claim 1, wherein
the non-volatile oil is at least one $C_{12}$-$C_{15}$ alkyl benzoate,
the solid cosmetic composition comprises 15% to 35% by weight of the $C_{12}$-$C_{15}$ alkyl benzoate, relative to a total weight of the solid cosmetic composition, and
the ratio between the amorphous hydrocarbon-based block copolymer to the $C_{12}$-$C_{15}$ alkyl benzoate is from 0.06 to 0.3.

18. The solid cosmetic composition according to claim 1, wherein the amorphous hydrocarbon-based block copolymer is selected from the group consisting of styrene-butylene/ethylene-styrene triblock copolymer, styrene-ethylene/butylene diblock copolymer, and mixtures thereof.

19. The solid cosmetic composition according to claim 1, wherein the pulverulent phase contains at least one nacre in an amount between 30% and 70% by weight relative to the total weight of the solid cosmetic composition.

20. The solid cosmetic composition according to claim 19, wherein the pulverulent phase contains from 50% to 90% by weight of nacre(s) relative to the total weight of the pulverulent phase.

21. The solid cosmetic composition according to claim 20,
wherein the solid cosmetic composition contains the at least one non-volatile oil in an amount of from 25% to 50% by weight relative to the total weight of the solid cosmetic composition.

* * * * *